(12) United States Patent
Butler

(10) Patent No.: US 10,045,952 B2
(45) Date of Patent: Aug. 14, 2018

(54) ANTI-VIRAL COMPOUND AND COMPOSITION

(71) Applicant: Forest Herbs Research Limited, Hamilton (NZ)

(72) Inventor: Peter Scott Butler, Hamilton (NZ)

(73) Assignee: Forest Herbs Research Limited, Nelson (NZ)

( * ) Notice: Subject to any disclaimer, the term of this patent is extended or adjusted under 35 U.S.C. 154(b) by 0 days.

(21) Appl. No.: 14/392,338

(22) PCT Filed: Jun. 25, 2014

(86) PCT No.: PCT/NZ2014/000127
§ 371 (c)(1),
(2) Date: Dec. 24, 2015

(87) PCT Pub. No.: WO2014/209136
PCT Pub. Date: Dec. 31, 2014

(65) Prior Publication Data
US 2016/0199318 A1   Jul. 14, 2016

(30) Foreign Application Priority Data
Jun. 25, 2013 (NZ) .................................. 612373

(51) Int. Cl.
| A61K 31/11 | (2006.01) |
| A61K 9/00 | (2006.01) |
| A61K 9/06 | (2006.01) |
| A61K 36/185 | (2006.01) |
| A61K 36/61 | (2006.01) |

(52) U.S. Cl.
CPC ............ *A61K 31/11* (2013.01); *A61K 9/0014* (2013.01); *A61K 9/06* (2013.01); *A61K 36/185* (2013.01); *A61K 36/61* (2013.01)

(58) Field of Classification Search
CPC ................................................... A61K 31/11
USPC ........................................................ 514/703
See application file for complete search history.

(56) References Cited

U.S. PATENT DOCUMENTS

| 5,523,105 | A | * | 6/1996 | Ishikawa | ................. | A23G 4/06 |
| | | | | | | 426/3 |
| 5,948,460 | A | | 9/1999 | Kang et al. | | |
| 2005/0158402 | A1 | | 7/2005 | Lee | | |

FOREIGN PATENT DOCUMENTS

| CN | 1554384 A | 12/2004 |
| CN | 101301451 A | 11/2008 |
| CN | 102885999 A | 1/2013 |
| JP | 64029307 | 1/1989 |
| JP | 4065005 B1 | 3/2008 |
| JP | 2010270097 | 12/2010 |
| JP | 20100270098 | 12/2010 |
| NZ | 520178 A | 2/2005 |
| WO | 2009065239 A1 | 5/2009 |

OTHER PUBLICATIONS

Maridass PASS: Prediction of activity spectra for biologically active constitent of polygodial (A dramane type of dialdehyde sequiterpene). Pharmacologyonline 3: 191-197 (2008) pp. 191-197.*
Parker et al., "Traditional dietary additives of the Maasai are antiviral against the measles virus", Journal of Ethnopharmacology 114, 2007, 146-152, Elsevier Ireland Ltd.
Saeidnia et al., "Biogenic trypanocidal sesquiterpenes: lead compounds to design future trypanocidal drugs a mini review", DARU Journal of Pharmaceutical Sciences 2013, 21:35.
Aaeeo et al., Polygodial, http://wikipedia.org/w/index.php?oldid=545016660.
Rosemary F. McCallion et al., "Antibiotic Substances From New Zealand Plants II. Polygodial, an Ani-Canada Agent From Pseudowintera Colorant", Journal of the Medicinal Plant Research, vol. 44, No. 3, Jan. 1, 1982, pp. 134-138.
Kubo et al.: "Polygodial, An Antifungal Potentiator", Journal of Natural Products, vol. 51, No. 1, Jan. 1, 1988, pp. 22-29.
Kumari A. et al.: "Protective Effect on oral natural phytonutrient in recurrent vulvovaginal candidiasis: A 12 month study", Journal of Biological regulators and homeostatic agents. vol. 25, No. 4, Oct. 1, 2011, pp. 543-551.
Nelson Zapata et al.: "The activity of a selected extract of Drimys winteri bark and polygodial on settling and probing behavior of the lettuce aphid Nasonovia ribisnigri", Phytoparasitica, vol. 38, No. 2, Feb. 24, 2010, pp. 191-199.
Kjirsten A. Wayman et al.: "Chemataxonomy of Pseudowintera sesquiterpene dialdehyde variants are species markers", Phytochemistry, vol. 71, No. 7, May 2010, pp. 766-772.
Asakawa et al.: "Distribution of Drimane sesquiterpenoids and tocopherols in liverworts, ferns and higher plants: *Polygonaceae, canellaceae* and *winteraceac* species", Natural Product Communications 2012 Natural Product Inc. USA, vol. 7, No. 6, 2012, pp. 685-692.
Zhou J., "Selection of Chinese Herbal Medicine Resources in Guangxi", Science Press, 2011, pp. 181-183.

* cited by examiner

*Primary Examiner* — Jennifer M Kim
(74) *Attorney, Agent, or Firm* — Gable Gotwals

(57) ABSTRACT

A use of polygodial or a structural derivative thereof, or a plant extract containing polygodial or a structural derivative thereof for the manufacture of a medicament for treating or preventing a viral infection, or a condition or disease resulting from a viral infection.

10 Claims, 4 Drawing Sheets

Note that where the quantity of uninfected cells is above 100% there may be some cell proliferation occurring

ANTI-VIRAL COMPOUND AND COMPOSITION

CROSS-REFERENCE TO RELATED APPLICATIONS

This application is the United States National Phase of Patent Application No. PCT/NZ2014/000127 filed 25 Jun. 2014, which claims priority to New Zealand Patent Application No. 612373 filed 25 Jun. 2013, each of which is incorporated herein by reference.

TECHNICAL FIELD

The present invention relates to an antiviral compound and composition to treat or prevent a viral infection in an animal.

BACKGROUND ART

Viruses that infect humans and other animals present a difficult and complex area of medical research. Viruses lead to a range of diseases which can manifest as a result of infection.

In humans, some of the more well known viruses include Human Immunodeficiency Virus (HIV), Hepatitis and Herpes viridae (more commonly known as the Herpes viruses, which are a large family of DNA viruses that cause diseases in animals).

Within the Herpes virus family, about five members are predominantly found in humans. It has been reported that about 90% of all adults have been infected with at least one of the five viruses listed below:
  Herpes simplex type 1 (HSV-1) which is known to cause orofacial lesions of a vesicular or ulcerative nature (i.e. cold-sores);
  Herpes simplex type 2 (HSV-2) the predominant cause of genital herpes (although noting there is some cross-over between HSV-2 and HSV-1 in the two regions);
  Varicella zoster virus which causes chicken-pox and shingles;
  Epstein-Barr virus which causes mononucleosis;
  Cytomegalovirus which causes symptoms similar to glandular fever.

HSV-1 and HSV-2 are of particular concern to humans not only due to their prevalence, but also their social implications. HSV-2 is spread through sexual contact, and is often seen through the eyes of the public as a disease of the promiscuous. Therefore, those with HSV-2 are burdened with a virus which not only has many negative social connotations associated with it, but also cannot currently be cured, is a significant discomfort during outbreaks, and is contagious.

In the case of HSV-1, it is often associated with HSV-2 and genital herpes even though the viruses are different. Therefore there is a negative implication associated with cold-sores, despite in many cases not being linked to genital herpes. Regardless, owing to the fact that facial cold-sores are in full public view on a person's face, the condition can cause significant distress to the sufferer as well as being a physical discomfort.

Beyond the negative social implications and discomfort of the diseases of HSV-1 and HSV-2, more serious consequences can result from the viral infections. Neonatal herpes infections can be severe with up to 50% mortality for disseminated infection. The risk is more severe if the mother has a primary infection during pregnancy with HSV-1. It is also possible that HSV-1 and HSV-2 can lead to infection in the cornea (herpetic keratitis) and brain (encephalitis), and can lead to illnesses in HIV patients.

There are treatments available for HSV-1 and HSV-2 to alleviate the symptoms and to appearance of the diseases caused by the virus. For example, antiviral medications acyclovir, valacyclovir and famiciclovir are used for recurrent herpes infections. Yet, these do not provide a cure and there are often significant side effects with treatment. For example, for treatment of HSV-2, oral medication is recommended for the treatment of genital herpes, but this comes at the expense of considerable side effects as outlined in Beauman, J G. Genital herpes: a review. *Am Fam Physician* 2005; 72:1527-1534.

A further problem can be increased drug resistance. In Strand et al., Antimicrobial Agents and Chemotherapy Vol 56, No 11, it states that "The need for antiviral agents is apparent, since HSV isolates resistant to acyclovir treatment are frequently isolated in immune-compromised patients".

Other treatments under research investigation include L-lysine, aspirin, or topical zinc treatment. Natural alternatives which are also under investigative studies include creams or gels containing licorice root (*Glycrrhiza glabra*), lemon balm (*Melissa officinalis*) or Aloe Vera (*Aloe barbadensis*). However, these approaches are still in their infancy and trials to support therapeutic effectiveness still need to be completed.

Although clinical trials are presently underway, there are still no vaccines currently available for Herpes simplex. Therefore, once a person is infected with the virus, he/she will be a carrier for life. Whilst some may present no or little symptoms, they still can infect others. Others, less fortunate, may present the disease phenotypes more frequently which can be a significant burden to the individual, both physically and emotionally.

A further problem with some compounds having anti-viral activity is that the compound can also displays strong cytotoxic characteristics. This means the compound kills host cells. Whilst this may be of benefit if the cell is infected with the virus, many compounds also are cytotoxic to healthy cells. For example, this disadvantageous trait is present in chemotherapy which by its very nature is cytotoxic.

Another problem which is seen with many anti-viral compounds, particularly for oral medications, is a low potency (often described as a high minimum inhibitory concentration, or MIC). This means that the patient must be administered higher amounts of the active compound to deliver the therapeutic result. This is disadvantageous as it can lead to more severe side effects from the compound or excipients in the medicament, can increase the cost and complexity of the manufacture of the medicament, and can lead to a lower shelf life of the product to due poor stability at higher concentrations. Therefore, there is a need to identify new compounds that have anti-viral activity and which preferably have a high potency, either on their own, or when synergistic combined with one or more other agents.

There has also been a focus over the past few decades to discover and use naturally available compounds as new anti-viral agents. The advantages of this approach can include:
  Often the compound, and/or the source of the compound (e.g. a plant) has been used for other purposes and thus has a proven safety record and good public perception.
  Avoids the need to do rational drug design which can cost significant amounts of research money and time.

A natural source of a compound or compounds is beneficial due to the ability to harvest large amounts of the source. Extracts of the source, or the pure compound(s) may then be used to develop suitable compositions and dosage regimes.

Knowledge of a naturally occurring compound displaying newly discovered anti-viral activity can be used as a platform for developing synthetic derivatives with improved pharmacokinetic features, such as improved potency, stability, or reduced side effects.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

DISCLOSURE OF THE INVENTION

According to one aspect of the present invention there is provided a use of polygodial or a structural derivative thereof for the manufacture of a medicament for treating or preventing a viral infection, or a condition or disease resulting from a viral infection.

According to a further aspect of the present invention there is provided a use of a plant extract containing polygodial or a structural derivative thereof for the manufacture of a medicament for to treating or preventing a viral infection, or a condition or disease resulting from a viral infection.

According to a further aspect of the present invention there is provided a use of a horopito extract for the manufacture of a medicament for treating or preventing a viral infection, or a condition or disease resulting from a viral infection.

According to a further aspect of the present invention there is provided a use of a composition containing polygodial or a structural derivative thereof, for the manufacture of a medicament for treating or preventing a viral infection, or a condition or disease resulting from a viral infection.

According to a further aspect of the present invention there is provided a use of polygodial or a structural derivative thereof for the treatment or prevention of a viral infection or an associated condition or disease.

According to a further aspect of the present invention there is provide a use of a horopito extract for the treatment or prevention of a viral infection or an associated condition or disease.

According to a further aspect of the present invention there is provided an anti-viral composition characterised in that the composition includes polygodial or a structural derivative thereof.

According to a further aspect of the present invention there is provided a method of treating or preventing a viral infection or a disease caused by the viral infection in an animal characterised in that the method includes administering to an animal in need thereof a therapeutic amount of polygodial or composition containing same as described substantially above.

According to a further aspect of the present invention there is provided a method of treating or preventing a viral infection or a disease caused by the viral infection in an animal characterised in that the method includes administering to an animal in need thereof a therapeutic amount of a horopito extract described substantially above.

The present invention is the surprising discovery and application that polygodial has anti-viral activity. Up until now, the substantial literature has disclosed polygodial only having anti-fungal activity, anti-microbial activity (limited to activity towards bacteria and yeast), antifeedent activity and molluscicidal activity.

Warburganal is structurally similar to polygodial and is also a drimane sesquiterpene dialdehyde compound. Like the other members of this class, both polygodial and warburganal are known to display anti-microbial and anti-fungal activity. Additionally, as identified in JP 19870724, warburganal is known to have anti-viral activity.

Yet warburganal is different to polygodial because it is particularly cytotoxic to (http://www.plantzafrica.com/med-monographs/warburgsal.pdf). As such, it is not typically applicable for most therapeutic uses (including anti-viral), other than as identified for anti-cancer therapies.

Also, Taniguchi et al., 1984 identifies that as a result of the structural difference between the warburganal and polygodial at position C9 (shown below), the antimicrobial activity between the two compounds is altered quite significantly.

Therefore it has been suggested that changes to the C9 substituents play an important part in the different antimicrobial effects of the two compounds.

The differences in structure and function, as clearly exemplified with regards to anti-microbial effects, has meant that someone skilled in the art would not have been motivated (and until now, accordingly has not) identified that polygodial has any amount of anti-viral activity.

It is thought that the cytotoxic characteristics of warburganal would have also deterred others in the industry from investigating related compounds in the broader class for non-cytotoxic anti-viral activity.

The inventors consider that, given the comparative lack of, or at least significantly lower, cytotoxicity exhibited by polygodial compared to that documented for warburganal, the use of polygodial provides a significant advancement in the field of natural anti-viral agents.

This class of compounds have been investigated and used for many years in relation to anti-fungal and anti-microbial activities. Even with prior knowledge of warburganal having anti-viral activity, it has only now been discovered by chance that polygodial advantageously has beneficial anti-viral effects. This opens up a commercially advantageous new use of polygodial.

Also, as will be further discussed further in the specification, there are many other advantages of polygodial as an anti-viral agent.

Throughout this specification the term "drimane sesquiterpene dialdehyde compound" should be taken as meaning any compound with the overall drimane sesquiterpene structure shown below, together with a dialdehyde group (structures below taken from Jansen and de Groot, 2004). Derita et al, Molecules 2013, 18, 2029-2051 highlights seventeen compounds that fall within the class of drimane sesquiterpenes, which can either be isolated from a natural source, or developed as derivatives.

Throughout this specification, the numbering in the drimane sesquiterpene structure below will be used to avoid confusion.

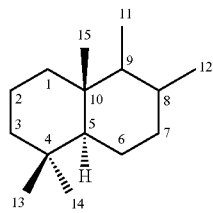

Drimane sesquiterpene skeleton

Throughout this specification the term "polygodial" should be taken as meaning any compound having the base structure shown below, having an aldehyde group at positions C8 and C9. This includes any isomers and structural derivatives of polygodial. Jansen and de Groot, 2004 outline a number of derivatives of polygodial and other related compounds within the broad drimane sesquiterpene dialdehyde compound class. Some of these include muzigadial, isotadeonal, ugandensidial and albicanol. These compounds and other similar derivatives of polygodial should be considered within the scope of the present invention.

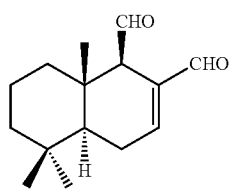

Structure of Polygodial

Throughout this specification the term "warburganal" should be taken as meaning any compound having the base structure shown below, having a hydroxyl group at position C9.

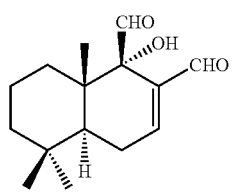

Structure of Warburganal

Preferred Features of the Present Invention

Throughout the present invention non-cytotoxic is a measurement of a compound or composition's toxicity to cells, regardless of whether the cells are virally infected or healthy uninfected cells. Cytotoxicity may be due to necrosis (cell death due to loss of cell membrane integrity), a decrease in cell viability where the cells stop growing and dividing, or apoptosis (genetically programmed cell death). In the present invention severe cytotoxicity is generally considered a negative attribute as the compound will have a toxic effect not only on the infected cells, but also the healthy cells.

A compound or composition according to the present invention with low cytotoxicity that still displays anti-viral effects may still be commercially beneficial. For instance, mild cytotoxicity may be quite helpful depending on how the antiviral is used e.g. topically, it may accelerate exfoliation of infected epithelial cells, and/or prevent an overzealous healing response of the type that leads to scarring.

If the present invention is used systemically (e.g. orally), then a reasonably high therapeutic index may be beneficial. A therapeutic index (T.I.) is defined by the minimum dose that is toxic to cells divided by the minimum dose that is toxic to virus. Particularly effective anti-viral drugs used systemically have a T.I. of 100-1000 or better (i.e. low cytotoxicity relative to a high potency to kill infected cells).

Initial studies have shown polygodial has low cytotoxicity at least to cells used in the in vitro testing for anti-viral activity. In the context of the present invention, this apparent lack or low level of cytotoxicity may be a significant improvement over warburganal. In some cases, cytotoxicity of warburganal has been considered a useful characteristic, for example if used for treating cancer. However, for the present application as an anti-viral agent, the apparent lower cytotoxicity may be seen as a significant advantage as it may not be killing healthy cells, or at least not to the same extent as warburganal.

As the inventors have identified in preliminary studies, the advantages of polygodial may include:

Preliminarily studies suggest polygodial is non-cytotoxic or at least has low toxicity compared to warbargunal, To exemplify this lack of cytotoxicity, we highlight that polygodial is present in East Asian spicy condiments.

Preliminary studies show that polygodial is highly potent, as will be elaborated below.

Preliminary studies suggest there may be a synergistic relationship between polygodial with other anti-viral agents such as those in tea-tree oil. This is particularly advantageous as the amount of polygodial may be reduced even lower whilst still providing a therapeutic effect (avoids possible burning sensation from polygodial, lowers manufacturing costs, etc).

It is likely that polygodial may be used as a therapeutic agent even after infection has taken place, or as a preventative anti-viral agent before infection.

Polygodial may be naturally sourced from a variety of plants etc, or can be synthetically derived, or manipulated to impart greater pharmacokinetic characteristics.

Polygodial is already used as a therapeutic compound (anti-fungal agent) and therefore is well understood in the industry, and is known to be safe.

Polygodial compositions may be applied topically (this may be a considerable advantage over systemic compositions). However other options such as systemically administered medicaments may also be applicable and advantageous.

In in vitro preliminary studies, polygodial is shown to be effective against HSV-1 and is likely to be effective towards other viruses such as HSV-2 as discussed below.

The use of polygodial provides a very advantageous new compound for treating viral infections such as cold sores or genital herpes, both of which are associated with many social and physical problems for sufferers.

Preferred Features of the Composition

Preferably, the composition includes naturally-derived polygodial. For example, polygodial may be extracted from Pseudowintera trees and shrubs (including *Pseudowintera colorata* also known as horopito), *Polygonum hydropiper* (Japanese name Yanagitade), Warburgia trees such as *Warburgia ugandensis* and *Warburgia stuhlmannii*, *Tasmannia lanceolate* (Mountain Pepper), *Tasmannia stipitata* (Dorrigo Pepper) Polygodial may also be sourced from a variety of other natural sources such as Canelo, Paracress and Waterpepper.

Alternatively, the composition includes semi- or fully-synthetic polygodial. This option may be applicable if polygodial is difficult to source in a particular geographical region, or if derivatisation of polygodial is required to boost pharmacokinetic characteristics (e.g. potency, stability).

Preferably, the composition includes polygodial which has been extracted from a naturally occurring plant.

Preferably, the composition includes polygodial sourced from horopito. Horopito is preferred because polygodial is found at high amounts in its leaves, and traditional use of horopito suggests its use is safe and well accepted by the public.

Preferably the composition includes a second anti-viral agent. The inventor has been able to ascertain that, through addition of at least one further anti-viral agent, synergistic effects may be achieved. This is exemplified in the preliminary studies with inclusion of a tea tree oil extract with horopito (the latter containing polygodial). The studies in Example 3 showed that Composition 1 (cream-based composition containing both horopito oleoresin and tea tree oil) had a lower MIC than the horopito oleoresin on its own (without tea tree oil), signifying a synergy.

Although only one preliminary test has been conducted, it may be assumed that synergistic effects with other anti-viral agents may be present; and that this should not be considered beyond the scope of the present invention.

Although the preliminary studies show polygodial is highly potent as an anti-viral agent against HSV-1, combination with other anti-viral agents may be commercially advantageous. This is because as a result of a synergistic effect, it may allow the overall amount of active agent in composition to be lowered, yet maintaining or improving the therapeutic effect of the composition. With polygodial in particular, a lower concentration may be particularly advantageous because it may cause a slight tingling or burning sensation when applied topically at higher concentrations.

Preferably, concentration of polygodial in the composition is between 0.0005% to 10% w/v.

Most preferably, the concentration of polygodial in the composition is approximately 0.001 to 5% w/v.

In preliminary studies, the Applicant has seen the $MIC_{50}$ for polygodial (concentration wherein 50% of cells are inhibited) is about 0.0075 to 0.015% w/v. This result was fairly consistent regardless of the different composition types as trialled. Clearly, if one were to rely on a synergistic effect with another anti-viral agent, the concentration of polygodial may be decreased even further.

Preferably, the composition is a cream.

Alternatively, the composition is a liquid spray, gel, foam, oil, or paste.

Preferably the composition includes excipients selected from the group consisting of a surfactant and/or an emulsifier, a stabiliser, an antioxidant, a preservative, and a pH modifier. Someone skilled in the art would appreciate the components which would be suitable to use in the composition. A particularly preferred composition and its method of manufacture is provided in the Best Modes Section.

Preferred Method of Treatment

The present invention may be used to treat substantially any animal or plant where an anti-viral effect is required.

Preferably, the method of treatment is for humans.

Preferably, the method of treatment is for treating or preventing conditions associated with infection of HSV-1 and HSV-2 viruses. For example, the present invention may be for the treatment or prevention of genital herpes and/or cold sores. This reflects that the inventors have identified through in vitro studies that polygodial and/or horopito extract is effective against HSV-1 virus. Due to the similarity to HSV-2 and in comparison to currently available drugs that are effective against both HSV-1 and HSV-2, one can reasonably expect that polygodial is similarly effective against HSV-2.

It should be understood that polygodial may also be used to treat other viruses beyond HSV-1 and HSV-2. For example, related viruses such as varicella zoster virus, Epstein-Barr virus and Cytomegalovirus may also be primary candidates for the present invention.

Preferably, the method of treatment includes topical application of the composition to the site of the condition. For example, the composition may be applied to the corners of the mouth in the case of a cold sore. Alternatively, the composition may be applied to the genital area in the case of genital herpes. In some cases, topical application may be a considerable advantage over systemic administration as currently used with other types of treatments for genital herpes.

However, the Applicant envisions that systemic (e.g. oral) administration may also be applicable and beneficial. For example, recent preliminary studies have suggested improved results may occur when both oral and topical applications are applied in tandem.

Also, it should be appreciated that different formulation types may be preferred for different applications.

Such variations in methods of delivery should not be considered beyond the scope of the invention.

Preferably, the method of treatment includes a dosage regime of applying between 0.1-5.0 mg/day of polygodial to the effected site.

BRIEF DESCRIPTION OF THE DRAWINGS

Further aspects of the present invention will become apparent from the ensuing description which is given by way of example only and with reference to the accompanying drawings in which.

BEST MODES FOR CARRYING OUT THE INVENTION

Figure 1:
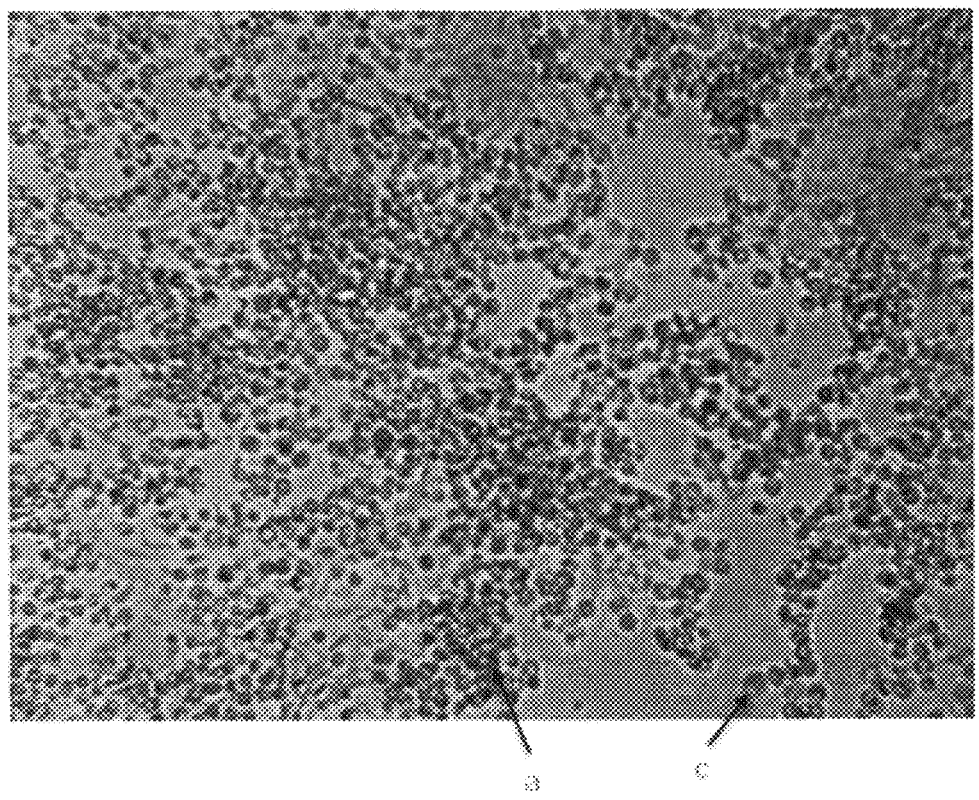
FIG. 1 Micrograph of cytopathic effect of Herpes simplex type 1 virus for Vero cells FIG. 2A Antiviral Activity of Polygodial against HSV-1 compared with pharmaceutical Acyclovir and virus only controls—Crystal Violet Assay using Vero Cells FIG. 2B Antiviral Activity of Polygodial against HSV-1 compared with pharmaceutical Acyclovir and virus only controls—Crystal Violet Assay using HaCaT Cells FIG. 3A Antiviral Activity of Horopito oleoresin against HSV-1 compared with pharmaceutical Acyclovir and virus only controls—Crystal Violet Assay using Vero Cells FIG. 3B Antiviral Activity of Horopito oleoresin against HSV-1 compared with pharmaceutical Acyclovir and virus only controls—Crystal Violet Assay using HaCaT Cells FIG. 4A/B Crystal violet assay results for different composition types.

Example 1: Example Anti-Viral Composition Containing Polygodial

| Component | Amount (% w/w) | Role |
|---|---|---|
| Composition 1: Cream-based composition | | |
| Horopito Oleoresin containing Polygodial | 1.5 horopito oleoresin (0.3 polygodial) | Active agent |
| Water | To volume | |
| Cetyl alcohol | 8.45 | Surfactant/emulsifier |
| Apricot kernel oil (*P armeniaca*) | 6.0 | Skin care |
| Tea Tree oil (*M. alternifolia*) | 3.0 | Active agent |
| Stearyl Alcohol | 1.25 | Stabiliser |
| Eumulgin B2 (Ceteareth-20) | 1.80 | Emulsifier |
| Lemon tea tree oil (*L. Petersonii*) | 1.0 | Active agent |
| Tocopherol acetate (Natural Source Vitamin E) | 0.5 | Antioxidant, skin care |
| *Aloe vera* extract 200 × 1 | 0.35 | Skin care |
| Potassium sorbate | 0.15 | preservative |
| Lactic acid | 0.1 | pH modifier |
| Composition 2: Oil-based composition | | |
| Horopito oleoresin | Approximately 10% w/w (containing approx. 20% w/w polygodial) | Active agent |
| Extra Virgin Olive Oil | Approximately 90% w/w | Carrier |
| Composition 3: Resin-based composition | | |
| Horopito Oleoresin | 100% containing approx. 20.0% w/w polygodial | Active agent |

Example 2: Method for Manufacturing the Cream-Based Composition

1. Prepare oil phase by heating Cetyl Alcohol, Stearyl Alcohol, Eumulgin B-2 and apricot kernel oil to 80° C. and add Tea Tree Oil and Vitamin E.
2. Mix Aloe Vera and Potassium Sorbate in water at 80° C.
3. Add the oil phase to the water phase and add the Lemon Tea Tree Oil.
4. Allow to cool.
5. Add oleoresin and adjust pH.

Example 3: Preliminary Trial Assessing Anti-Viral Activity of Three Exemplary Polygodial Compositions in Example 1 Against Herpes Simplex Type 1 Virus (HSV-1)

This study assessed the effectiveness of three trial compositions (see Example 1) containing various amounts of polygodial compared to a commercially available product, Acyclovir, which is therapeutically used to treat HSV-1 related cold sores.

In the examples illustrated in FIGS. 2 and 3, pure polygodial and Horopito oleoresin (extract of horopito leaves) were tested against Acyclovir.

In the example illustrated in FIG. 4, the resin-based, oil-based and cream-based compositions were comparatively assessed.

1. Methods 1.1 Culture and Titration of HSV-1

A wild-type HSV-1 obtained from ESR, Upper Hutt, was cultured in Vero (African Green Monkey kidney) tissue culture cells. HSV-1 virus was added to confluent Vero cell monolayers and allowed to infect until >70% cytopathic effect was observed. The infected cultures were then frozen and thawed three times and centrifuged at 3000 rpm for 15 minutes. The supernatant was stored at −80° C. until use. Our virus was found to contain $8.5×10^6$ viral particles/ml and an infection rate of $8.5×10^4$ particles was used for all further assays.

1.2. Crystal Violet Assay

The crystal violet assay depends on the ability of adherent cell lines such as Vero to stick to the bottom of tissue culture plates. Damaged or dead cells lose their ability to adhere and are removed during a washing process. Viable cells remaining are stained with crystal violet, which is then released from the cells and measured in a spectrophotometer.

Vero cells were seeded at $3×10^5$ cells/ml overnight at 37° C. in 96-well tissue culture plates. When cells had reached confluency, 50 μl of the growth media was removed and replaced with 25 μl of virus and 25 μl of test product. Controls were the same as those used in the xCelligence assay. The assay was terminated after 96 hours which is the length of time taken to see CPE in the control wells.

2. Results and Discussion 2.1 Culture and Titration of HSV-1

With reference to FIG. 1, when inoculated into Vero cells, the HSV-1 preparation received from ESR was found to produce cell damage (cytopathic effect; CPE) with rounding and detachment of the cell monolayer as shown as (a). Uninfected cells remained transparent and flattened (b). Enlarged cells (ballooning) can also be seen as (c) but are more evident earlier in the infection process. This type of CPE is typical of Herpes simplex virus infection.

2.2 Crystal Violet Assay

Figure 2A:
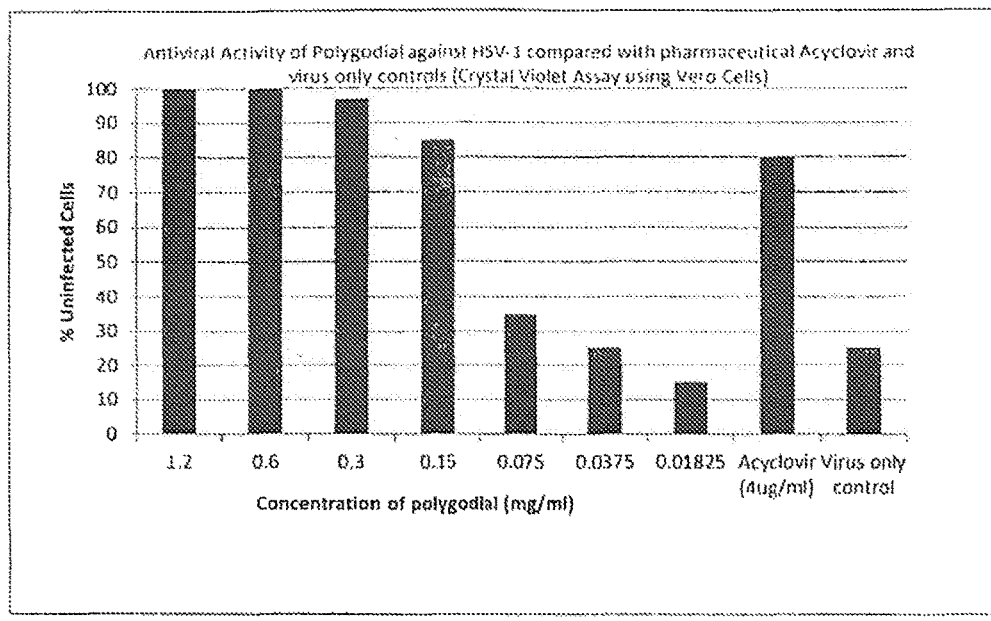
Figure 3A:
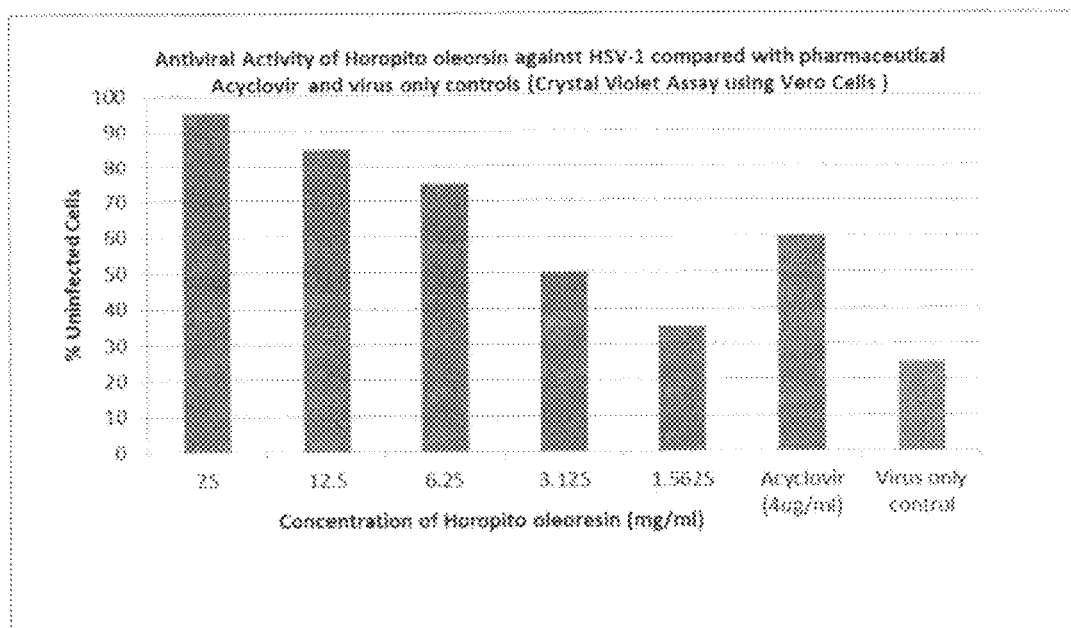

The results of the crystal violet assay for pure polygodial and horopito oleoresin are shown in FIGS. 2A and B, and 3A and B, respectively.

The alcohol used as a solvent for the compositions had no effect on the Vero cells at the concentration used in the products. In the cells only control (negative control; not shown) and acyclovir treated healthy cells (antiviral control; not shown), Vero cells remained healthy and viable throughout the experiments.

Comparison of Anti-Viral Activity of Polygodial and Horopito Oleoresin

Figure 2B:
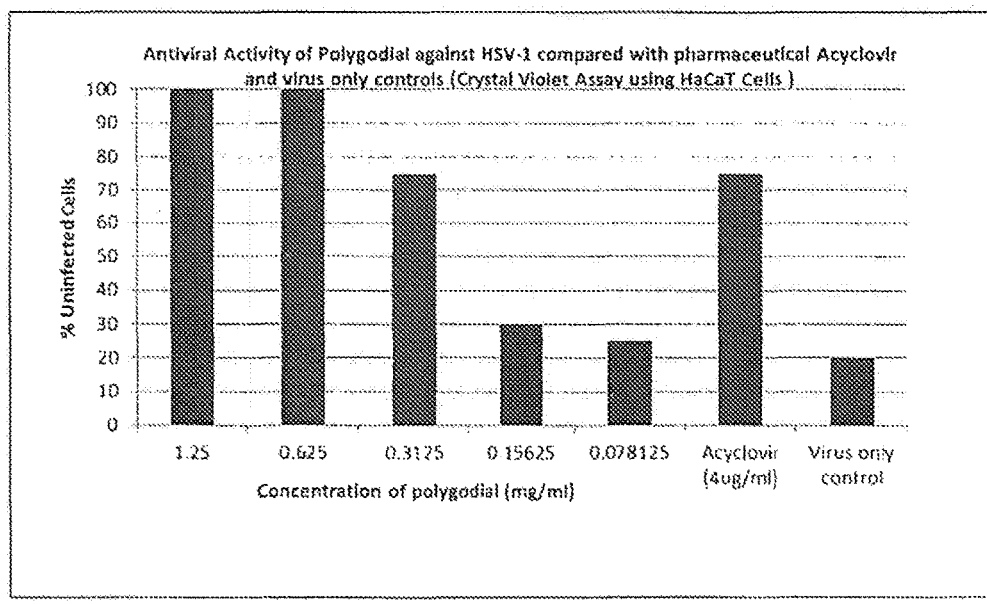

In the first test (results shown in FIGS. 2A and B), the HSV-1 anti-viral activity of pure polygodial was assessed in comparison to Acyclovir in both Vero cells (FIG. 2A) and HaCaT cells (FIG. 2B). The virus only control showed an infection rate of about 80%. In the Acyclovir control, 4 μl/ml of Acyclovir resulted in 80% uninfected cells.

As can be seen in Vero Cells and HaCaT cells, the anti-viral effect of polygodial at a concentration of 0.15 mg/ml and 0.3125 mg/ml, respectively, was comparative to the effect seen with treatment of 4 μl/ml Acyclovir. The MIC of polygodial was calculated at 0.6 to 1.2 mg/ml.

In this test, it was confirmed that polygodial is not cytotoxic at the concentrations tested because where strong anti-viral activity is present, the cells are alive and uninfected by the virus.

Figure 3B:
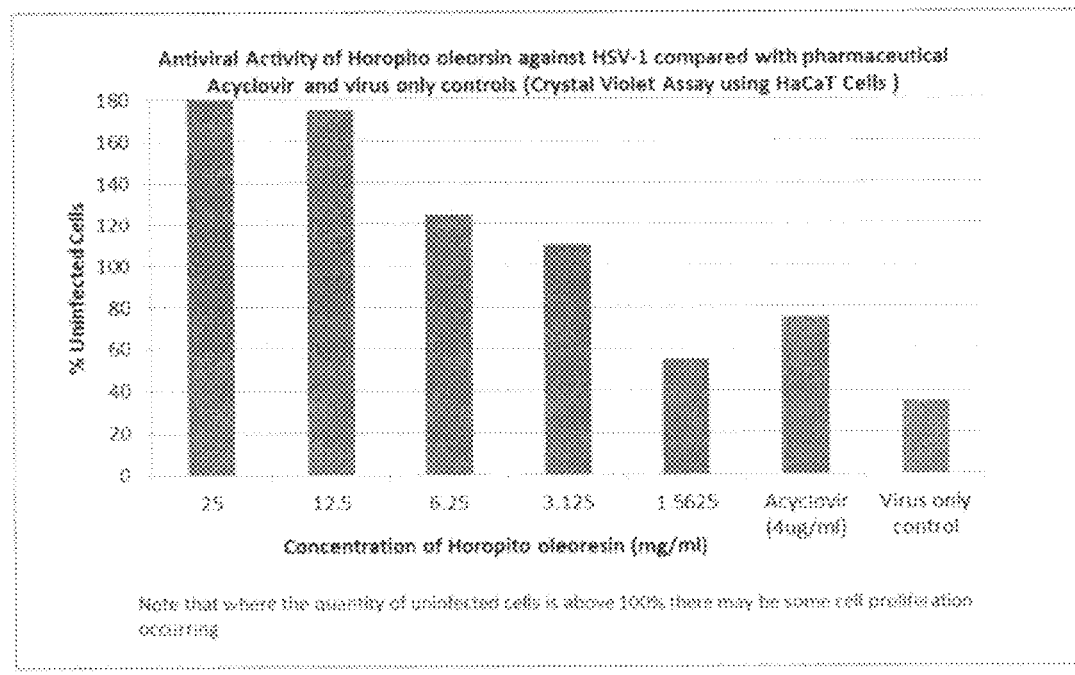

In the second test (results shown in FIGS. 3A and B), the HSV-1 anti-viral activity of Horopito oleoresin was assessed in comparison to Acyclovir in both Vero cells (FIG. 3A) and HaCaT cells (FIG. 3B). The virus only control showed that an infection rate of about 75%. In the Acyclovir control, 4 μl/ml of Acyclovir resulted in 60% uninfected Vero cells and 75% uninfected HaCaT cells.

As can be seen in Vero Cells and HaCaT cells, the anti-viral effect of Horopito oleoresin at a concentration of about 4 mg/ml and 2 mg/ml, respectively, was comparative to the effect seen with treatment of 4 μl/ml Acyclovir. The MIC of Horopito oleoresin was calculated between 0.625 to 6.25 mg/ml.

In this test, it was confirmed that Horopito oleoresin is not cytotoxic at the concentrations tested because where strong anti-viral activity is present, the cells are alive and uninfected by the virus.

Serial Dilution Test of Resin-Based, Oil-Based and Cream Based Compositions

Using serial dilutions of the compositions shown in Example 1, at the working concentration of 10% weight/volume and a further 1/10 dilution (1%), the cream and resin-based compositions had a completely inhibitory effect on HSV-1.

Figure 4A:
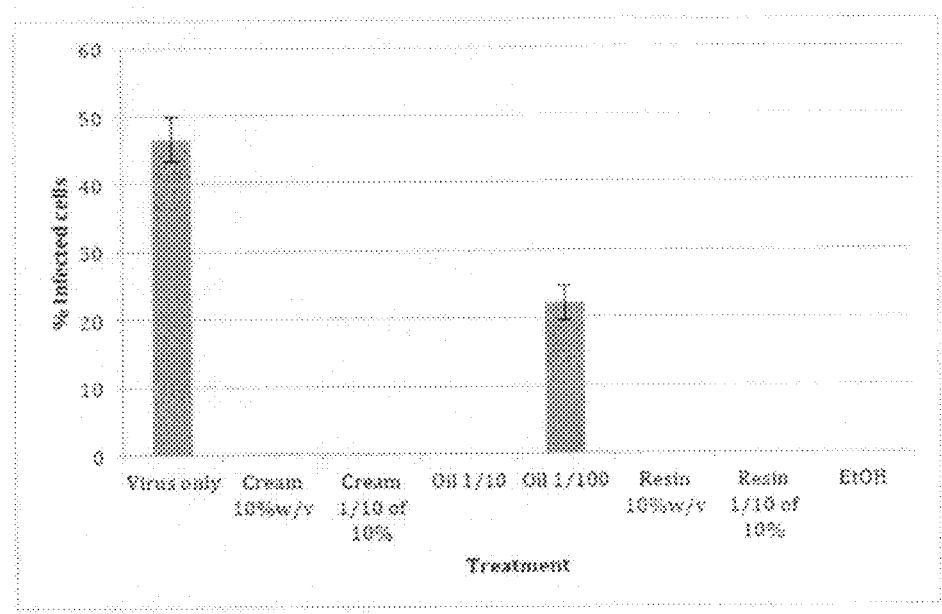

Similarly, the oil-based (oleoresin in olive oil) composition was tested at 10% and 1% serial dilutions of the stock composition. As shown in FIG. 4A, the oil-based composition was to completely inhibitory at 10% but only partially at 1%. The "dilution factor" in FIGS. 4A and B corresponds to the dilution applied to the 10% working solution concentration; e.g. cream 1/80 is a 1 to 80 dilution of a solution of 10 g of cream diluted to 100 ml.

This is a very interesting result as the cream-based composition actually contained less polygodial than the oil-based composition. This suggests that a synergistic effect is occurring in the cream involving the polygodial and anti-viral agent's in the tea tree oil/s.

A second crystal violet assay experiment was performed to determine the preliminary minimum inhibitory concentrations (MIC) for HSV-1 for each of the three test compositions. Results are also shown in Table 1 below.

TABLE 1

Minimum and 50% Inhibitory Concentrations of Products against HSV-1 in the Crystal Violet Assay

| Product | Minimum Inhibitory Concentration | Approximate 50% inhibitory concentration |
| --- | --- | --- |
| Cream based composition | 1% | 0.25% |
| Oil based composition | 1% | Between 1 and 0.5% |
| Resin-based composition | <0.0625% | <0.0625% |

Figure 4B:
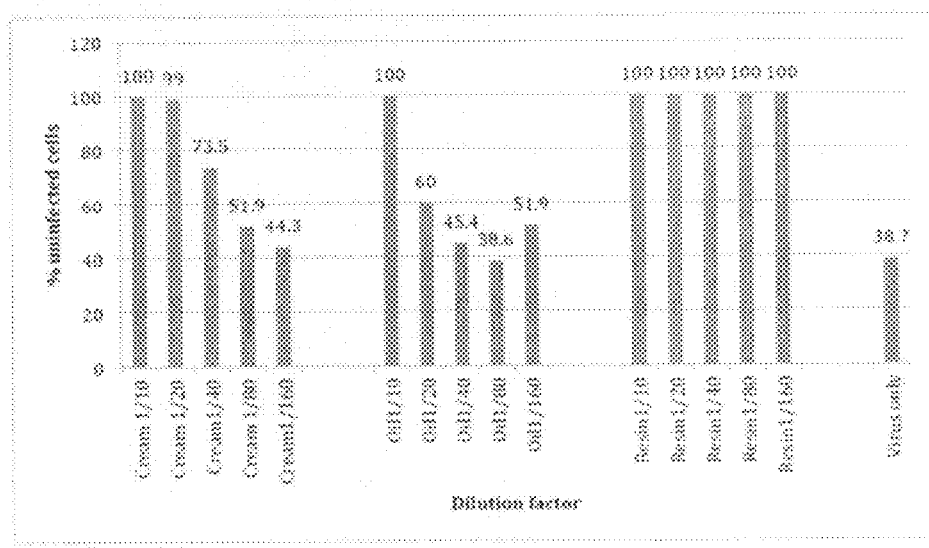

As illustrated in FIG. 4b, an infection rate of 61.3% was achieved (virus only bar).

For the cream-based composition, a dose response was seen as the inhibitory effect decreased uniformly until it was practically negated at 1/160 dilution of the working concentration solution. The MIC of the working concentration (10% w/v) of the cream-based composition was 1/10 (absolute concentration 1% of the cream product), with partial inhibition detectable down to the 1/80 dilution (FIG. 4b). Based on the starting concentration of polygodial in the cream-based composition, this composition had an $MIC_{50}$ of approximately 0.001% w/v polygodial or 10 mg/L (ppm).

The MIC of the oil-based composition was approximately 1/10 dilution of the 10% working concentration solution in Example 1. There was significant partial inhibition at 1/20 dilution of the working concentration solution. The paradoxical increase in inhibition seen with the final dilution is unexplained, but not unknown and may be related to dissociation of components of the oil. Based on the starting concentration of polygodial in the oil-based composition, this composition had an $MIC_{50}$ of 0.0125% w/v polygodial or 100 mg/L (100 ppm).

The MIC of the resin-based composition was not achieved and this product was completely inhibitory for HSV-1 at all the dilutions tested. This is not surprising as the starting concentration of polygodial in this composition was 20% w/v.

Aspects of the present invention have been described by way of example only and it should be appreciated that modifications and additions may be made thereto without departing from the scope thereof as defined in the appended claims.

What I claim is:

1. A method of treating a viral infection or a disease or condition caused by the viral infection in an animal, wherein the viral infection is from Herpes simplex type 1 (HSV-1) or Herpes simplex type 2 (HSV-2), the method comprises administering to an animal in need thereof a therapeutic amount of polygodial of formula I

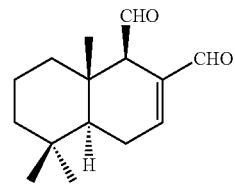

or a therapeutic amount of a horopito (*Pseudowintera colorata*) extract containing polygodial of formula I, or a composition containing same.

2. The method as claimed in claim 1 wherein the polygodial is derived from a horopito (*Pseudowintera colorata*) plant or close plant relative thereof.

3. The method as claimed in claim 1 wherein the composition comprises a second anti-viral agent derived from tea tree oil, or a tea tree oil extract.

4. The method as claimed in claim 1 wherein the concentration of polygodial in the composition is between 0.0005% to 10% w/v.

5. The method as claimed in claim 1 wherein the composition is formulated or the polygodial is administered as a cream, liquid spray, gel, foam, oil, or paste.

6. The method as claimed in claim 1 wherein the composition includes one or more excipients selected from the group consisting of a surfactant and an emulsifier, a stabiliser, an antioxidant, a preservative, and a pH modifier.

7. The method as claimed in claim 1 wherein the administration is by topical application to the site of the viral infection or the condition or disease resulting from the viral infection.

8. The method as claimed in claim 1 wherein the administration is topical administration.

9. The method as claimed in claim 1 wherein the administration is topical application to the genital herpes or the one or more cold sores.

10. The method as claimed in claim 1 wherein the disease or condition caused by the viral infection is genital herpes or one or more cold sores.

\* \* \* \* \*